(12) United States Patent
Agarwal et al.

(10) Patent No.: US 9,278,928 B2
(45) Date of Patent: Mar. 8, 2016

(54) PROCESS FOR THE PREPARATION OF D-THREO-RITALINIC ACID SALTS VIA NOVEL SALTS OF INTERMEDIATE THEREOF

(71) Applicant: ZCL CHEMICALS LIMITED, Mumbai (IN)

(72) Inventors: Nand Lal Agarwal, Bharuch (IN); Rahul Arunbhai Bhavsar, Bharuch (IN); Kunal Kamleshbhai Pathak, Bharuch (IN)

(73) Assignee: ZCL CHEMICALS LIMITED, Mumbai, Maharashtra (IN)

( * ) Notice: Subject to any disclaimer, the term of this patent is extended or adjusted under 35 U.S.C. 154(b) by 0 days.

(21) Appl. No.: 14/415,742

(22) PCT Filed: Oct. 21, 2013

(86) PCT No.: PCT/IN2013/000642
§ 371 (c)(1),
(2) Date: Jan. 20, 2015

(87) PCT Pub. No.: WO2014/083572
PCT Pub. Date: Jun. 5, 2014

(65) Prior Publication Data
US 2015/0259290 A1   Sep. 17, 2015

(30) Foreign Application Priority Data
Nov. 29, 2012 (IN) .......................... 3391/MUM/2012

(51) Int. Cl.
*C07D 211/34* (2006.01)

(52) U.S. Cl.
CPC .................................... *C07D 211/34* (2013.01)

(58) Field of Classification Search
CPC ..................................................... C07D 211/34
USPC .......................................................... 546/238
See application file for complete search history.

(56) References Cited

U.S. PATENT DOCUMENTS

| 2,957,880 | A | * | 10/1960 | Rometsch | ...................... 546/233 |
| 4,002,666 | A | * | 1/1977 | Shirai et al. | ..................... 560/29 |
| 6,441,178 | B2 | * | 8/2002 | Zavareh et al. | ............... 546/238 |
| 2015/0038720 | A1 | * | 2/2015 | Huntley et al. | ............... 546/238 |

OTHER PUBLICATIONS

Berge "Pharmaceutial salts" J. Pharm Sci. 66(1) 1-19 (1977).*
PharmAcid, CrysEngComm supplement p. 1 (2005).*

* cited by examiner

*Primary Examiner* — Celia Chang
(74) *Attorney, Agent, or Firm* — Prakash Nama; Global IP Services, PLLC

(57) ABSTRACT

The present invention relates to a process for the preparation of d-threo-ritalinic acid salt thereof. More particularly, the present invention relates a process for the preparation of d-threo-ritalinic acid salt via novel organic salts of intermediate thereof.

16 Claims, No Drawings

PROCESS FOR THE PREPARATION OF D-THREO-RITALINIC ACID SALTS VIA NOVEL SALTS OF INTERMEDIATE THEREOF

FIELD OF THE INVENTION

The present invention relates to a process for the preparation of d-threo-ritalinic acid and its salts thereof. Particularly, the present invention relates to a process for the preparation of d-threo-ritalinic acid salts via its novel salts of intermediate thereof.

BACKGROUND OF THE INVENTION

The chemical name of dexmethylphenidate hydrochloride is (2R)-phenyl-[(2R)-piperidyl-2-yl-acetic acid methyl ester hydrochloride and it is also known as d-threo-enantiomer of methylphenidate hydrochloride. Methylphenidate hydrochloride is a mixture of dl-threo racemates and it is prescribed as psychostimulant. Dexmethylphenidate marketed as its hydrochloride salt, under the brand name "Focalin". Subsequence study of methylphenidate hydrochloride revealed that its two enantiomers i.e. dl-threo methylphenidate hydrochloride and d-threo enantiomers are considered to be active disclosed in Biochemistry Pharmacology 1961, 8, 263-268. It is used in treatment of Attention Deficient Hyperactivity Disorder (ADHD). Further, OPRD 2000, 4, 55-59 mentions that (R,R) enantiomer of methylphenidate (dexmethylphenidate) is about 5 to 38 times more active than its corresponding (S,S) enantiomer of methylphenidate.

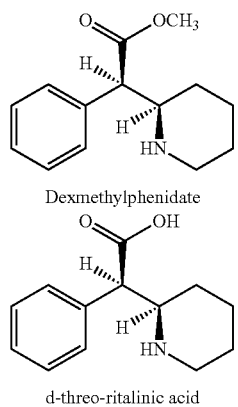

U.S. Pat. No. 2,957,880 discloses a process for preparing methylphenidate as a mixture of the erythro [R*, S*] and threo [R*, R*] racemates. Also discloses threo isomer of ritalinic acid prepared from the corresponding acid amide, in which resolution of amide using d-tartaric acid converted to (R,R)-ritalinic acid in three steps.

Another several methods are reported for the resolution of dl-threo-methylphenidate by using expensive resolving agent like 1,1'-binaphthyl-2,2'-diyl hydrogen phosphate. Other resolving agents like O,O-diaroyltartaric acid or menthoxy-acetic acid or dibenzoyl-D-tartaric acid are disclosed in WO09727176, GB97/00643, U.S. Pat. Nos. 6,100,401, 6,121,453, 6,162,919 and 6,242,464 for the resolution of dl-threo-methylphenidate. Resolution of threo-methylphenidate may also be achieved by enzymatic hydrolysis methods proposed by Prashad (1998) [U.S. Pat. No. 7,247,730] and in WO98/25902. The main drawbacks of the above cited processes are resolution at the final stage may leads to poor enantiomeric purity and further need to be purified. The additional steps of purification may make the process expensive and tedious. In addition, the enzymatic hydrolysis is time consuming process and may affect the fast output of the product.

U.S. Pat. No. 6,441,178 discloses the resolution of dl-threo-ritalinic acid salt. The resolution performed by treating dl-threo-ritalinic acid hydrochloride with (−)-1-phenylethylamine in large volume of ethanol gives only 77% ee diasteromeric salt enriched in d-threo-ritalinic acid.

U.S. Pat. No. 7,247,730 discloses a process for the preparation of threo-N-Boc-ritalinic acid from the methylphenidate in three steps using crystalline sodium N-Boc-threo-ritalinate as precursor.

US 2011/0130569 discloses a process for the preparation of the d-threo-ritalinic acid. dl-threo-ritalinic acid treated with (+)-dibenzoyl-D-tartaric acid as resolving agent in large volume of solvents mixture of methanol/water to get d-threo-ritalinic acid-dibenzoyl tartaric acid salt. Thus obtained salt treated with 35% hydrochloric acid in mixture of toluene and water, concentrated under vacuum and isolated by treating with acetone. The volume of resolution solvent used herein is quite higher.

Hence, there is a need to provide an industrially viable process for the preparation of d-threo-ritalinic acid salt via its novel salts of intermediate avoiding large volume of solvents at resolution stage resulted in very good purity and yield which further helps in increasing the purity and yield of the final product i.e. dexmethylphenidate hydrochloride.

OBJECTIVE OF THE INVENTION

The principal objective of the present invention is to provide an efficient and industrially feasible process for preparation of d-threo-ritalinic acid and its salts thereof.

Another main objective of the invention is to provide a process for preparation of d-threo-ritalinic acid and its salts thereof which circumvents the need of using large volume of solvents at the resolution stage.

Another objective of the present invention is to overcome or ameliorate at least one of the disadvantages of the prior art, or to provide a useful alternative.

Still another objective of the invention is to provide a process for preparation of d-threo-ritalinic acid salt via its novel salts of intermediate thereof.

Further objective of the invention is to provide an environment friendly process for the preparation of d-threo-ritalinic acid and its salts thereof.

Further more objective of the present invention is to provide d-threo-ritalinic acid and its salts thereof having high purity and yield.

Yet another objective of the invention is to provide substantially pure d-threo-ritalinic acid and its salts thereof can be converted to dexmethylphenidate hydrochloride.

SUMMARY OF THE INVENTION

According to principle aspect, the present invention provides a process for the preparation of d-threo-ritalinic acid and its salts thereof, which proves to be eco-friendly and industrially viable. The process comprises the steps of:
   a). treating dl-threo-ritalinic acid with organic acid in suitable solvent;
   b). optionally isolating organic acid salt of dl-threo-ritalinic acid;

c). resolving organic acid salt of dl-threo-ritalinic acid obtained from step b) with resolving agent;

d). treating chiral acid salt of d-threo-ritalinic acid obtained from step c) with strong acid; and e). isolating acid salt of d-threo-ritalinic acid.

According to another aspect, the present invention provides a process for preparation of d-threo-ritalinic acid salt via its novel salts of intermediate thereof.

According to another aspect, the present invention provides d-threo-ritalinic acid and its salts thereof having high purity and yield.

According to another aspect, the present invention provides a process for preparation of acid salt of d-threo-ritalinic acid comprises the step of; treating free acid of d-threo-ritalinic acid with acid to form salt of d-threo-ritalinic acid.

According to another aspect, the present invention provides a process for preparation of substantially pure d-threo-ritalinic acid which is useful in the preparation of dexmethylphenidate hydrochloride.

DETAILED DESCRIPTION OF THE INVENTION

As used herein, the term "ambient temperature" describing common indoor temperatures usually falls in the range of 25 to 35° C.

As used herein, the term "reflux temperature" describing the boiling temperature of solvents.

As used herein, the term "substantially pure" refers to the substance having a chiral purity of greater than about 99%, specifically greater than about 99.5%, more specifically greater than about 99.8%, and still more specifically greater than about 99.9%.

All ranges recited herein include the endpoints, including those that recite a range "between" two values. Terms such as "about", "generally" and the like are to be construed as modifying a term or value such that it is not an absolute. Such terms will be defined by the circumstances and the terms that they modify as those terms are understood by those skill in the art. This includes, at very least, the degree of expected experimental error, technique error and instrument error for a given technique used to measure a value.

The present invention provides an efficient process for the preparation of d-threo-ritalinic acid salts.

According to the embodiment of the invention provides an industrially viable process for preparation of d-threo-ritalinic acid salt starting from dl-threo-ritalinic acid.

Stage 1:

dl-Threo-ritalinic acid can be reacted with organic acid in suitable solvent to form an organic acid salt of dl-threo-ritalinic acid. Generally, the reaction involves organic acid salt formation of dl-threo-ritalinic acid by reacting dl-threo-ritalinic acid with organic acid in suitable solvents. Suitable solvent include, but are not limited to lower alcohol such as methanol, ethanol, n-propanol, isopropanol and/or water and the like in any suitable proportion or any ratio. Organic acid include oxalic acid, malic acid, malonic acid, citric acid, tartaric acid, fumaric acid and the like. The reaction mixture is stirred for 1 to 12 hours, preferably for 1-3 hours, more preferably till the completion of the reaction at reflux to ambient temperature, preferably at ambient temperature. The organic acid salt of dl-threo-ritalinic acid can optionally be isolated from the reaction mixture by suitable techniques such as filtration or centrifugation and the like. Dried the compound by the conventional techniques know in the art. The process resulted in desired compound in high purity and yield. Alternatively, formed organic acid salt of dl-threo-ritalinic acid can be carried forward to the next stage.

Particularly, dl-threo-ritalinic acid is reacted with the organic acid such as oxalic acid in the mixture of alcohol and water, preferably methanol and water, more preferably in ratio of 1:0.88. The reaction mixture is stirred for about 1 hour at temperature about 25-30° C. After completion of the reaction, the same is filtered and distilled out at temperature 60-70° C. under the reduced pressure till the stirrable semi-solid obtained. The ketonic solvent, preferably acetone is added in obtained residue and stirred for about 4 hours at temperature about 25-30° C. The precipitated oxalate salt of dl-threo-ritalinic acid is washed with acetone and the salt formation is confirmed by the elemental analysis.

In another way, after treating dl-threo-ritalinic acid with organic acid such as oxalic acid in the mixture of alcohol and water, the reaction mixture can be taken for the next stage in-situ.

Stage 2:

The organic acid salt of dl-threo-ritalinic acid in isolated form or in-situ can be reacted with resolving agent in suitable solvent to form chiral acid salt of dl-threo-ritalinic acid. Generally, the reaction involves chiral acid salt formation of dl-threo-ritalinic acid by reacting organic acid salt of dl-threo-ritalinic acid with chiral acid in suitable solvent. Organic acid include oxalic acid, malic acid, malonic acid, citric acid, tartaric acid, fumaric acid and the like. In another way, the reaction can be defined by a salt replacement or salt exchange. The process involves replacement of organic acid salt by chiral acid salt in reaction media. Suitable solvent include, but are not limited to lower alcohol such as methanol, ethanol, n-propanol, isopropanol and/or water and the like in any suitable proportion or any ratio, preferably 20-30 times, more preferably 10-15 times, most preferably 5-10 times. Chiral acid include (+)-dibenzoyl-D-tartaric acid and the like. The reaction mixture is heated for 1 to 12 hours, preferably for 1-3 hours, more preferably at reflux to ambient temperature, most preferably at reflux temperature followed by cooling the reaction mixture. The precipitated chiral acid salt of d-threo-ritalinic acid can optionally be isolated from the reaction mixture by suitable techniques such as filtration or centrifugation and the like. Dried the compound by the conventional techniques know in the art. The confirmation of the desired chiral compound can be done by measuring specific optical rotation. The process resulted in desired compound in high purity and yield. In another aspect, the use of resolving agents such as (−)-dibenzoyl-L-tartaric acid persuade the desired compound in mother liquor.

Particularly, organic acid salts such as oxalate salt of dl-threo-ritalinic acid in isolated form or in-situ can be reacted with the chiral acid such as (+)-dibenzoyl-D-tartaric acid in suitable solvent as described in above stage 1. The resulted reaction mixture is heated to reflux temperature and maintained for 1 hour. The reaction mixture is cooled to ambient temperature and stirred for 6-10 hours, preferably 8 hours. Further cooled to 5-10° C. and stirred for 1 hour. The material precipitated is (+)-dibenzoyl-D-tartaric acid salt of d-threo-ritalinic acid and the another part which is (+)-dibenzoyl-D-tartaric acid salt of l-threo-ritalinic acid will remain in mother liquor. It is observed by the scientists of the present invention that the undesired compound (+)-dibenzoyl-D-tartaric acid salt of l-threo-ritalinic acid and detached oxalic acid is having high solubility in alcohol:water. Hence that part remains in the mother liquor. The desired compound (+)-dibenzoyl-D-tartaric acid salt of d-threo-ritalinic acid filtered off and washed with methanol:water.

One of the major attracting feature over the prior art is substantial reduction of solvent volume makes the process environment friendly, higher the productivity, higher the purity and yield. In another way, large volume of solvent needs big size reactor at the plant level for the reaction which also lowers the output of the product. Handling large volume of solvent is very difficult and tedious procedure. The present invention significantly reduces the volume of solvent gives outstanding output and handling ease at the plant level. It is known that solvent reduction can be increased the batch size which saves the manpower, time and energy consumption. Discarding of large volume of aqueous solvent can be hazardous to the environment and also needs lengthy procedure of effluent treatment in accordance with very high COD (Chemical oxygen demand). All the advantages cumulatively make the present invention plant friendly and cost-effective. For example comparison of the present invention process with US patent application 2011/0130569 A1 with respect to volume of solvent used is depicted in below table.

| | Methanol: Water Comparison between US 2011/0130569 & Present Invention | | |
|---|---|---|---|
| Solvent | US 2011/0130569 as per Example 1 used volume | Present Invention as per Example 1 used volume | Reduction of Volume |
| In Reaction Methanol | 21 V | 4.5 V | 78% reduced in RM* |
| Water | 16 V | 4.0 V | 75% reduced in RM* |
| In Washing Methanol | 1 V | 2 V | |
| Water | 1 V | 2 V | |
| Total Volume Methanol | 22 V | 6.5 V | 70% reduced over all |
| Water | 17 V | 6.0 V | 65% reduced over all |

*RM is defined as "Reaction mixture"

Stage 3:

The chiral acid salt of d-threo-ritalinic acid can be treated with acid in suitable solvent to form salt of d-threo-ritalinic acid. Generally, the reaction involves salt formation of d-threo-ritalinic acid by reacting chiral acid salt of d-threo-ritalinic acid with acid in suitable solvent. Suitable solvent can be mixture of hydrocarbon and water in any suitable proportion or any ratio; preferably in mixture of toluene and water; more preferably in the ratio of 2.25:1. "Acid salt of d-threo-ritalinic acid" include inorganic acid can be selected from hydrochloric acid, hydrobromic acid, phosphoric acid; organic acid can be selected from oxalic acid, malic acid, malonic acid, citric acid, tartaric acid, fumaric acid and the like. Preferably hydrochloric acid includes gaseous hydrochloric acid, concentrated hydrochloric acid, aqueous hydrochloric acid, alcoholic hydrochloric acid and the like. The reaction mixture is stirred up to the completion of addition of acid. The reaction mixture heated under reduced pressure at temperature about 50-100° C., preferably at 60-70° C. for 1 to 12 hours, preferably till the stirrable semisolid residue obtained. The traces of the solvent can be removed by stripping and degassing under reduced pressure. For the work-up procedure, the second solvent is added into the obtained residue at temperature about 50-70° C., preferably 50-55° C. and maintained for 1-3 hours, preferably 0.5 to 1 hour. Second solvent include ketonic solvent such as acetone, methyl ethyl ketone, methyl isobutyl ketone and the like. The reaction mixture is cooled at temperature about 20-35° C., preferably at about 20-25° C. and stirred for 1-3 hours, preferably 2 hours and further cooled at temperature about 0-20° C., preferably 15-20° C. The compound can be isolated from the reaction mixture by suitable techniques such as filtration or centrifugation and the like. Dried the compound by the conventional techniques know in the art. The process resulted in desired compound in high purity and yield.

Particularly, The chiral acid salt of d-threo-ritalinic acid such as dibenzoyl-D-tartrate salt of d-threo-ritalinic acid is treated with acid such as concentrated hydrochloric acid in suitable solvent such as mixture of toluene:water in ratio of 2.25:1. The concentrated hydrochloric acid is added into the reaction mixture under stirring. After completion of the addition, the reaction mixture is heated at temperature about 60-70° C. under reduced pressure till the stirrable semisolid residue remains. The obtained residue is stripped by toluene at temperature about 60-70° C. and degassed to remove the traces of water. Thereafter acetone is added to the residue and maintained for 30 minutes at temperature about 50-55° C. The reaction mixture is cooled to 20-25° C. and stirred for 2 hours. Further cooled to 15-20° C. and stirred for 1 hour. The precipitated material is filtered, washed and dried to give pure hydrochloric acid salt of d-threo-ritalinic acid.

In another embodiment, the acid salt of d-threo-ritalinic acid can be converted into the free acid form by breaking the salt using conventional methods or as prepared in present invention. Wherein starting acid salt of d-threo-ritalinic acid is strong acid salt. "Strong acid" include hydrochloric acid, hydrobromic acid, phosphoric acid and the like. The free acid in isolated form or in-situ can be treated with the acid include hydrochloric acid, hydrobromic acid, phosphoric acid, oxalic acid, malic acid, malonic acid, citric acid, tartaric acid, fumaric acid and the like to prepare the acid salt of d-threo-ritalinic acid.

Particularly, the acid salt of d-threo-ritalinic acid such as hydrochloric acid salt of d-threo-ritalinic acid can be converted to free acid form of d-threo-ritalinic acid by reacting with base include inorganic base or organic base; in solvent include water, alcohol, ketone, nitrile, ethers or mixture thereof. Obtained free acid form of d-threo-ritalinic acid in isolated form or in-situ can be further treated with acid include hydrobromic acid, oxalic acid, malic acid, malonic acid, citric acid, tartaric acid, fumaric acid and the like, preferably oxalic acid in solvent include water, alcohol, ketone, nitrile or mixture thereof and the like, preferably mixture of alcohol and water. Isolation of salt of d-threo-ritalinic acid can be done by means of any conventional techniques or the reaction mixture stirred for about 1 hour at temperature about 25-30° C. After completion of the reaction, the same is filtered and distilled out at temperature 60-70° C. under the reduced pressure till the stirrable semisolid obtained. The ether such as dimethylether, diethylether, diisopropyl ether, preferably diisopropyl ether is added in obtained residue and stirred for about 4 hours at temperature about 25-30° C. The precipitated acid salt of d-threo-ritalinic acid such as oxalate salt of d-threo-ritalinic acid is washed with acetone to remove excess acid and the salt formation is confirmed by the elemental analysis.

Yet another embodiment, the chiral acid salt of l-threo-ritalinic acid can be converted to d-threo-ritalinic acid by racemization technique. Particularly, chiral acid salt of l-threo-ritalinic acid can be isolated in free form followed by racemization using conventional techniques known in the art and further can be converted to d-threo-ritalinic acid salts as described in the present invention.

The obtained d-threo-ritalinic acid salt by the present invention can be converted to dexmethylphenidate and its salts thereof.

The Scheme of the Present Invention is as Depicted Below:

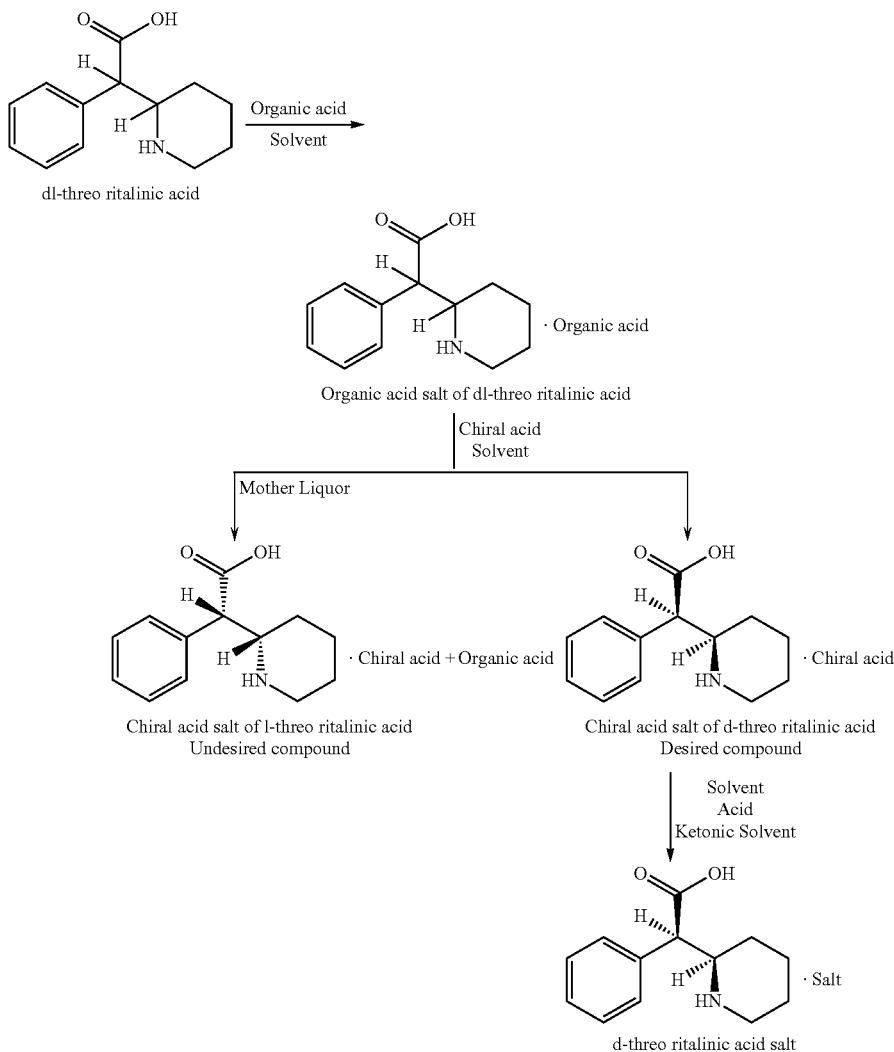

The invention is further defined by reference to the following examples describing in detail by the preparation of the compounds of the invention. It will be apparent to those skilled in the art that many modifications, both to materials and methods, may be practiced without departing from the scope of the invention.

EXAMPLES

Example 1

Preparation of Dibenzoyl-D-Tartaric Acid Salt of d-Threo-Ritalinic Acid dl-threo-ritalinic acid (100 gm; 0.456 mole) was charged in the mixture of methanol (450 ml; 4.5 v/w) and water (400 ml; 4 v/w) under stirring. Oxalic acid (80.45 gm; 0.638 mole) was added in the reaction mass and stirred for 1 hour at 25-30° C. (+) Dibenzoyl-D-tartaric acid (182 gm; 0.483 mole) was added in the reaction mass at 25-30° C. The resulting mass was heated to reflux at temperature 65-70° C. and maintained for 1 hour. The mass was then gradually cooled to 20-25° C. and maintained for 8 hours at the same temperature. The reaction mass was cooled to 5-10° C. and stirred for 1 hour. The precipitated material was filtered and washed with methanol:water (200 ml×2) (1:1) mixture to yield 132 gm of desired dibenzoyl-D-tartrate salt of d-threo-ritalinic acid. Yield: 100%, Melting point: 92-98° C.; SOR $[\alpha]_D^{20}$: (+)90.0° (C=1.0% w/v in methanol), Purity by HPLC: >99.0%

Example 2

Preparation of d-Threo-Ritalinic Acid Hydrochloride

Dibenzoyl-D-tartaric acid salt of d-threo-ritalinic acid (132 gm; 0.228 mole), toluene (225 ml, 2.25 v/w), water (100 ml, 1.0 w/w) were charged into the reaction assembly. Hydrochloric acid (40 gm, 30-35%) was added under stirring. The reaction mixture distilled at 60-70° C. under reduced pressure completely till the stirrable semisolid residue remained. To remove traces of water, toluene (200 ml) stripping was done at 60-70° C. and degassed it under reduced pressure. Acetone (300 ml) was added in the residue at 50-55° C. within 20-30 minutes and maintained the temperature for 30 min. The reaction mass was cooled to 20-25° C. and stirred for 2 hours.

Further it was cooled to 15-20° C. and stirred for 1 hour. The precipitated solid was filtered off and washed with acetone (100 ml) to yield 48 gm of desired d-threo-ritalinic acid hydrochloride. Yield: 82%, Melting Point: 222-226° C., SOR $[\alpha]_D^{20}$: +90.0° (C=2.0% w/v in methanol), Purity by HPLC: >99.5%, Chiral Purity: 100%

Example 3

Isolation of dl-Threo-Ritalinic Acid Oxalate Salt dl-threo-ritalinic acid (50 gm; 0.228 mole) was charged in the mixture of methanol (225 ml; 4.5 v/w) and water (200 ml; 4 v/w) under stirring. Oxalic acid (40.2 gm; 0.319 mole) was added into the reaction mass and stirred at temperature 25-30° C. for 1 hour. The reaction mass was filtered and distilled out at 60-70° C. under reduced pressure till the stirrable semisolid obtained. Acetone (300 ml; 6 v/w) was added in the obtained residue and stirred for 4 hours at 25-30° C. Precipitated solid was then filtered off and washed with acetone (50 ml; 1 v/w). The product was dried at temperature 45-50° C. to get 56 gm of oxalate salt of dl-threo-ritalinic acid. Oxalate salt formation was confirmed by elemental analysis. Yield: 79%, Melting Point: 164.1-170.7° C., Elemental analysis: Theoretical C (58.25), H (6.19), N (4.53), O (31.04); Actual C (59.23), H (7.33), N (4.65), and O (30.28).

Spectroscopic Interpretation: $^1$H NMR (DMSO-$d_6$, 400 MHz) ($\delta_H$): 1.3-1.7 (6H, m, —$CH_2$ of piperidyl ring); 2.9-2.96 (2H, t, —$CH_2$ of piperidyl ring); 3.62-3.66 (1H, q, —CH of piperidyl ring); 3.84 to 3.86 (1H, d, proton of —CH—COOH); 7.10-7.37 (5H, m, CH of aromatic ring).

IR ($cm^{-1}$) (KBr): 3171 (O—H str. of —COOH); 2575, 2508 (N—H str.); 1742 (C=O str. Of —COOH); 1530, 1491 (Benzenoid bands); 1375 (C—N str.); 1150 (C—O str. of —COOH)

Other salts of dl-threo-ritalinic acid were prepared as method given above and resulted as depicted in below table:

| Example | Acid Used | % Yield | Analysis |
|---|---|---|---|
| 4 | Citric acid | 81.81% | SOR: (+)90.95° |
| 5 | Malic acid | 45.45% | SOR: (+)93.34° |
| 6 | Tartaric acid | 100% | SOR: (+)89.61° |
| 7 | Malonic acid | 100% | SOR: (+)93.33° |
| 8 | Fumaric acid | 100% | SOR: (+)92.52° |

Example 4

Isolation of d-Threo-Ritalinic Acid Oxalate Salt d-Threo-ritalinic acid hydrochloride (50 gm) was added in water (200 ml) and stirred it to clear. The pH of reaction mass was adjusted between 4.0-6.5 using Liq. $NH_3$ (~20%). Reaction mass was maintained for 1 hour at 20-25° C. The reaction mass was distilled 50% under reduced pressure at 60-70° C. and was cooled to 20-25° C., The reaction mass was stirred for 1 hour. The product was filtered at 4.0-6.5 pH and suck dried to afford 30 gm free acid of d-threo-ritalinic acid.

Free acid of d-threo-ritalinic acid (obtained above) was added in the mixture of methanol (135 ml; 4.5 v/w) and water (120 ml; 4 v/w) under stirring. Oxalic acid (24.15 gm; 1.4 mole) was added in the reaction mass and stirred at 25-30° C. for 1 hour. Reaction mass was filtered and distilled off at 60-70° C. under reduced pressure till the stirrable semisolid obtained. Diisopropyl ether (60 ml; 2 v/w) was added in the obtained residue and stirred for 4 hour at 25-30° C. Precipitated solid was then filtered. Wet cake was washed properly with acetone (60 ml; 2 v/w) two times. Product was dried at 45-50° C. to get 32 gm of oxalate salt of d-threo-ritalinic acid of. Oxalate salt formation was confirmed by Elemental analysis, IR spectra and NMR spectra. Yield: 53%, Melting Point: 166-168° C., SOR $[\alpha]_D^{20}$: +67.0° (C=2.0% w/v in methanol) Elemental analysis: Theoretical C (58.25), H (6.19), N (4.53), O (31.04); Actual C (59.20), H (6.68), N (4.70), and O (30.30).

Spectroscopic Interpretation: $^1$H NMR (DMSO-d6, 400 MHz) ($\delta_H$): 1.31 to 1.69 (6H, m, —$CH_2$ of piperidyl ring); 2.90 to 2.97 (2H, t, —$CH_2$ of piperidyl ring): 3.61 to 3.65 (1H, q, —CH of piperidyl ring); 3.83 to 3.85 (1H, d, proton of —CH—COOH); 7.04 to 7.35 (5H, m, CH of aromatic ring).

IR ($cm^{-1}$) (KBr): 3162 (O—H str. of —COOH); 2863, 2885 (N—H str.); 1699 (C=O str. Of —COOH); 1498, 1435 (Benzenoid bands); 1331 (C—N str.); 1153 (C—O str. of —COOH)

We claim:
1. A process for the preparation of d-threo-ritalinic acid and its salts thereof, comprising the steps of:
   a). treating di-threo-ritalinic acid with organic acid selected from oxalic acid, malic acid, malonic acid, citric acid and fumaric acid in suitable solvent to form organic acid salt of dl-threo-ritalinic acid;
   b). resolving the organic acid salt of dl-threo-ritalinic acid with resolving agent to form chiral acid salt of d-threo-ritalinic acid;
   c). treating the chiral acid salt of d-threo-ritalinic acid with strong acid to form d-threo-ritalinic acid salt; and
   d). isolating the d-threo-ritalinic acid salt.
2. The process according to claim 1, wherein in step a) the suitable solvent is selected from lower alcohol such as methanol, ethanol, n-propanol, isopropanol and/or water in any suitable proportion or any ratio.
3. The process according to claim 2, wherein the suitable solvent is mixture of methanol:water.
4. The process according to claim 3, wherein the methanol:water used is 5-10 times.
5. The process according to claim 1, wherein in step b) the resolving agent is selected from (+)-dibenzoyl-D-tartaric acid, and (−)-dibenzoyl-L-tartaric acid.
6. The process according to claim 1, wherein in step c) the strong acid is selected from hydrochloric acid, hydrobromic acid, and phosphoric acid.
7. The process according to claim 1. wherein the d-threo-ritalinic acid and its salts thereof having chiral purity more than 99.9%.
8. Organic acid salts of dl-threo-ritalinic acid; wherein organic salt is selected from oxalate, malate, malonate, or fumarate.
9. Acid salt of d-threo-ritalinic acid, wherein acid is selected from oxalic acid, malic acid, malonic acid, citric acid, and fumaric acid.
10. The acid salt of d-threo-ritalinic acid according to claim 9, wherein the acid salt of d-threo-ritalinic acid is prepared by treating free acid of d-threo-ritalinic acid with acid in a solvent or mixture of solvent.
11. A process for the preparation of d-threo-ritalinic acid and its salts thereof, comprising the steps of:
   a). treating dl-threo-ritalinic acid with organic acid selected from oxalic acid, malic acid, malonic acid, citric acid and fumaric acid in suitable solvent to form organic acid salt of dl-threo-ritalinic acid;
   b). isolating the organic acid salt of dl-threo-ritalinic acid;

c). resolving the organic acid salt of dl-threo-ritalinic acid with resolving agent to form chiral acid salt of d-threo-ritalinic acid;

d). treating the chiral acid salt of d-threo-ritalinic acid with strong acid to form d-threo-ritalinic acid salt; and e). isolating the d-threo-ritalinic acid salt.

12. The process according to claim 11, wherein in step a) the suitable solvent is selected from lower alcohol such as methanol, ethanol, n-propanol, isopropanol and/or water in any suitable proportion or any ratio.

13. The process according to claim 12, wherein the suitable solvent is mixture of methanol:water.

14. The process according to claim 13, wherein the methanol:water used is 5-10 times.

15. The process according to claim 11, wherein in step c) the resolving agent is selected from (+)-dibenzoyl-D-tartaric acid and (−)-dibenzoyl-L-tartaric acid.

16. The process according to claim 11, wherein in step d) the strong acid is selected from hydrochloric acid, hydrobromic acid, and phosphoric acid.

* * * * *